United States Patent
Bayat et al.

(10) Patent No.: US 10,359,480 B2
(45) Date of Patent: Jul. 23, 2019

(54) OPTICALLY DETECTED MAGNETIC RESONANCE IMAGING WITH AN ELECTROMAGNETIC FIELD RESONATOR

(71) Applicant: President and Fellows of Harvard College, Cambridge, MA (US)

(72) Inventors: Khadijeh Bayat, Watertown, MA (US); Marko Loncar, Belmont, MA (US)

(73) Assignee: PRESIDENTS AND FELLOWS OF HARVARD COLLEGE, Cambridge, MA (US)

( * ) Notice: Subject to any disclaimer, the term of this patent is extended or adjusted under 35 U.S.C. 154(b) by 256 days.

(21) Appl. No.: 15/117,796

(22) PCT Filed: Feb. 13, 2015

(86) PCT No.: PCT/US2015/015762
§ 371 (c)(1),
(2) Date: Aug. 10, 2016

(87) PCT Pub. No.: WO2015/175047
PCT Pub. Date: Nov. 19, 2015

(65) Prior Publication Data
US 2017/0010338 A1    Jan. 12, 2017

Related U.S. Application Data

(60) Provisional application No. 61/939,337, filed on Feb. 13, 2014.

(51) Int. Cl.
*G01N 1/00* (2006.01)
*G02B 1/00* (2006.01)
(Continued)

(52) U.S. Cl.
CPC .......... *G01R 33/323* (2013.01); *G01R 33/62* (2013.01); *G01N 1/00* (2013.01); *G01N 2201/00* (2013.01); *G02B 1/00* (2013.01)

(58) Field of Classification Search
CPC ........ G01N 1/00; G01N 2201/00; G02B 1/00; G02B 2207/00; C12Q 1/00; C12Q 2304/00
See application file for complete search history.

(56) References Cited

U.S. PATENT DOCUMENTS 5,789,257 A * 8/1998 Tapper .................. G01R 33/46
324/300
7,446,880 B2 * 11/2008 Vollmer ................. G01N 21/23
356/480

(Continued)

OTHER PUBLICATIONS

Al-Naib et al., "Coplanar Waveguides Incorporating SRRS or CSRRS," Progress in Electromagnetics Research B, vol. 23, 343-355 (2010).

(Continued)

*Primary Examiner* — Jermele M Hollington
*Assistant Examiner* — Temilade S Rhodes-Vivour
(74) *Attorney, Agent, or Firm* — Occhiuti & Rohlicek LLP (57) ABSTRACT

Measuring a sample includes providing a magnetic field at the sample using an electromagnetic field resonator. The electromagnetic field resonator includes two or more resonant structures at least partially contained within dielectric material of a substrate, at least a first resonant structure configured to provide the magnetic field at the sample positioned in proximity to the first resonant structure. The sample is characterized by an electron spin resonance frequency. A size of an inner area of the first resonant structure and a number of resonant structures included in the electromagnetic field resonator at least partially determine a range of an operating resonance frequency of the electromagnetic field resonator that includes the electron spin resonance frequency. Measuring the sample also includes receiving an output optical signal from the sample generated based at least in part on a magnetic field generated by the electromagnetic field resonator.

18 Claims, 5 Drawing Sheets

(51) Int. Cl.
G01R 33/32 (2006.01)
G01R 33/62 (2006.01)

(56) References Cited

U.S. PATENT DOCUMENTS

| | | | |
|---|---|---|---|
| 7,826,504 B2 | 11/2010 | Chen et al. | |
| 8,193,808 B2 | 6/2012 | Fu et al. | |
| 2006/0227331 A1* | 10/2006 | Vollmer | G01N 21/23 356/483 |
| 2012/0074936 A1* | 3/2012 | Kayano | G01R 33/3621 324/307 |
| 2013/0093424 A1 | 4/2013 | Blank et al. | |
| 2013/0157283 A1* | 6/2013 | Yung | B01L 3/502761 435/7.1 |
| 2014/0218032 A1* | 8/2014 | Mohebbi | G01R 33/60 324/316 |

OTHER PUBLICATIONS

Annino et al., "High Frequency Single-Mode Resonators for EPR Spectroscopy Enabling Rotations of the Sample About Two Orthogonal Axes," Apr. 22, 2005, pp. 1-19.

De Lange et al., "Controlling the Quantum Dynamics of a Mesoscopic Spin Bath in Diamond,"arXiv:1104.4648v2 [quant-ph] (2012) all pages.

Hardy et al., "Split-Ring Resonator for Use in Magnetic Resonance from 200-2000 MHz," Rev. Sci. Instrum. 52(2), Feb. 1981, pp. 213-216.

Katsarakis et al., "Electric Coupling to the Magnetic Resonance of Split Ring Resonators," Applied Physics Letters, vol. 84, No. 15, Apr. 12, 2004, pp. 2943-2945.

Momo et al., "On the Design of a Split Ring Resonator for ESR Spectroscopy Between 1 and 4 GHz," J. Phys. E: Sci. Instrum., vol. 16 (1983) pp. 43-46.

Neumann et al., "Excited-State Spectroscopy of Single Nv Defect in Diamond Using Optically Detected Magnetic Resonance," arXiv:0807.2379v2 [quant-ph] Feb. 10, 2009, all pages.

Sakran et al., "Electron Spin Resonance Microscopic Surface Imaging Using a Microwave Scanning Probe," Applied Physics Letters, vol. 82, No. 9, Mar. 3, 2003, pp. 1479-1481.

Stanwix et al., "Coherence of Nitrogen-vacancy Electronic Spin Ensembles in Diamond," Physical Review B, 82, 201201(R) (2010).

Yanwu et al., "Propagation Characteristics of Complementary Split-Ring Resonators Excited by Internal Cylindrical Wave," arXiv:1201.1254v2 [physics.optics] Jan. 9, 2012, all pages.

Zhurbenko et al., "Analytical Model for Double Split Ring Resonators with Arbitrary Ring Width," *Microwave and Optical Technology Letters*, vol. 50, No. 2, Feb. 2008, all pages.

* cited by examiner

Table 1

| Parameter | Value | Parameter | Value |
|---|---|---|---|
| $\varepsilon_r$ | 10.2 | $w$ | 1 mm |
| $t_{Cu}$ | 9 μm | $g_c$ | 0.05 mm |
| tan(δ) | 0.0023 | $g_r$ | 0.2 mm |
| $r_1$ | 1.2 mm | $g_s$ | 0.4 mm |
| $r_2$ | 2.4 mm | | |

…
OPTICALLY DETECTED MAGNETIC RESONANCE IMAGING WITH AN ELECTROMAGNETIC FIELD RESONATOR

CROSS-REFERENCE TO RELATED APPLICATIONS

This application is the National Stage of International Application No. PCT/US2015/015762, filed on Feb. 13, 2015, which claims priority to U.S. Ser. No. 61/939,337, filed on Feb. 13, 2014, the contents of which are hereby incorporated herein by reference in their entirety.

STATEMENT AS TO FEDERALLY SPONSORED RESEARCH

This invention was made with government support under the following grant: HR011-11-C-0073 from Defense Advanced Research Projects Agency (DARPA). The government has certain rights in the invention.

BACKGROUND

This description relates to optically detected magnetic resonance imaging with an electromagnetic field resonator. The negatively charged Nitrogen-Vacancy (NV) center is an attractive platform for magnetic sensing. One technique that can be used to perform magnetic sensing of the NV center is Optically Detected Magnetic Resonance (ODMR) imaging. Moreover, an NV-based magnetic sensor works under ambient conditions and is bio-compatible, which make it a great candidate for bio-imaging. However, a variety of shortcomings in the imaging system may limit the precision and sensitivity with which the imaging can be performed.

SUMMARY

In one aspect, in general, an apparatus includes: a substrate including a dielectric material; an electromagnetic field resonator including two or more resonant structures at least partially contained within the dielectric material, at least a first resonant structure configured to provide a magnetic field at a sample positioned in proximity to the first resonant structure, the sample being characterized by an electron spin resonance frequency, wherein a size of an inner area of the first resonant structure and a number of resonant structures included in the electromagnetic field resonator at least partially determine a range of an operating resonance frequency of the electromagnetic field resonator that includes the electron spin resonance frequency; and an optical coupler positioned in proximity to the first resonant structure, and configured to receive an output optical signal from the sample, the output optical signal being generated based at least in part on a magnetic field generated by the electromagnetic field resonator.

Aspects can include one or more of the following features.

The apparatus further includes a tuning element configured to tune the operating resonance frequency of the electromagnetic field resonator within the range.

The first resonant structure is configured to at least partially surround the sample within the inner area of the first resonant structure.

The range of the operating resonance frequency includes at least some microwave frequencies.

The size of the inner area provides a uniformity of the magnetic field generated by the electromagnetic field resonator within about 10% or less over an area of the sample of about one square millimeter or more.

The two or more resonant structures comprise two or more split rings.

The substrate comprises a printed circuit board.

The apparatus further includes an optical coupler configured to receive an output optical signal from the sample, the output optical signal being generated based at least in part on a magnetic field generated by the electromagnetic field resonator.

The optical coupler is further configured to provide an input optical signal to the sample.

The apparatus further includes a microwave coupler configured to couple a microwave signal into the electromagnetic field resonator.

The apparatus further includes a microwave source configured to provide a pulsed microwave signal to the microwave coupler, with a bandwidth of the pulsed microwave signal being within a bandwidth of the electromagnetic field resonator.

The apparatus further includes a tuning element configured to tune the bandwidth of the electromagnetic field resonator.

The tuning element comprises a material that changes a quality factor of the electromagnetic field resonator.

The sample comprises diamond, and the electron spin resonance frequency is based on nitrogen-vacancy centers in the diamond.

The sample comprises a thin-film material.

The first resonant structure is configured to provide a magnetic field at the sample positioned in proximity to a first side of the electromagnetic field resonator; and the optical coupler is positioned in proximity to a second side of the electromagnetic field resonator, and is configured to receive the output optical signal from the sample through an opening defined by the first resonant structure.

The sample is positioned within a cryogenic chamber.

In another aspect, in general, a method for measuring a sample includes: providing a magnetic field at the sample using an electromagnetic field resonator including two or more resonant structures at least partially contained within dielectric material of a substrate, at least a first resonant structure configured to provide the magnetic field at the sample positioned in proximity to the first resonant structure, the sample being characterized by an electron spin resonance frequency, wherein a size of an inner area of the first resonant structure and a number of resonant structures included in the electromagnetic field resonator at least partially determine a range of an operating resonance frequency of the electromagnetic field resonator that includes the electron spin resonance frequency; and receiving an output optical signal from the sample using an optical coupler positioned in proximity to the first resonant structure, the output optical signal being generated based at least in part on a magnetic field generated by the electromagnetic field resonator.

Aspects can have one or more of the following advantages.

The techniques described herein generally relate to optically detectable magnetic resonance imaging that enables detecting small magnetic fields under ambient conditions. For example, ODMR imaging of NV centers in diamond over volumes on the order of a few $mm^3$ is enabled using a double split-ring microwave resonator as a highly efficient microwave delivery circuitry.

The techniques described herein relate to a device for efficient, uniform and large area microwave magnetic field coupling to NV centers in diamond for ODMR imaging, precision magnetometry and bio-imaging applications. In some embodiments, the device includes a double split-ring resonator made on a substrate such as a printed circuit board (PCB). This device enhances the microwave magnetic field coupling to NV centers. Moreover, the device delivers highly uniform microwave magnetic field over areas on the order of a few mm$^2$ with low variance (e.g., less than 5% variance). It also facilitates large area access to NV centers and ODMR imaging of the diamond and paves the way for precision optical magnetometry where a large volume of NVs can be addressed at once, or where large samples are the subject of ODMR characterization.

A variety of types of applications are enabled by the techniques described herein:

Precision ultrasensitive magnetometry at ambient condition

Magnetic field imaging with high resolution over wide area

ODMR imaging on biological samples with mm range dimensions

ODMR imaging in presence of highly photoluminescence materials such as organic molecules Temperature imaging over a wide area Strain imaging over a wide area Electric field imaging over a wide area A variety of types of measurement systems (including hardware and control circuitry or software modules) can be constructed, including:

A system for highly efficient coupling of microwave signal to NV centers in diamond A system for large area (mm$^2$) coupling of microwave signal to NV centers in diamond A system for uniform coupling of microwave signal to NV centers in diamond over large volume (mm$^3$)

A system for high resolution optically detectable spin resonance imaging over large area A system for high resolution optically detectable spin resonance imaging of NV centers in diamond over large area A system for 2D electron spin resonance imaging of NV centers in diamond over mm$^2$ area A system for 3D electron spin resonance imaging of NV centers in diamond over mm$^3$ volume A system for high resolution optically detectable spin resonance imaging of NV centers in diamond implanted biological samples A system for high resolution optically detectable spin resonance imaging of NV centers in diamond implanted mixed photoluminescent A system for sub-micron molecular imaging by optically detected spin resonance imaging of NV centers in diamond A system for nondestructive and contactless high resolution ODMR imaging of NV centers in diamond A system for room temperature and high precision magnetic sensing with a sensitivity of fT/$\sqrt{\text{Hz}}$ Other features and advantages of the invention are apparent from the following description, and from the claims.

DESCRIPTION

In one aspect, the ODMR imaging techniques are applied to the development and utilization of an electromagnetic field resonator for uniform and efficient coupling of microwave magnetic field into NV centers in diamond over a relatively large area (e.g., on the order of 1 mm$^2$). Various aspects of the techniques will be illustrated with reference to experimental results using an example of a particular embodiment of an electromagnetic field resonator (i.e., a double split-ring microwave resonator). The experimental results are for illustrative purposes only, and other embodiments may exhibit other results and characteristics. Uniformity and magnitude of delivered microwave magnetic field was measured using a Rabi nutation experiment on arrays of diamond nanowires with ensemble NV centers. An average Rabi nutation frequency of 15.65 MHz was measured over an area of 0.95 mm×1.2 mm, for an input microwave power of 0.5 W. By mapping the Rabi nutation frequency to the magnetic field, the average value of the magnetic field over the aforementioned area and input microwave power was 5.59 G with a standard deviation of 0.24 G.

To coherently manipulate the spin state of NV for magnetic sensing, electromagnetic field at the frequencies near to that of Electron Spin Resonance (ESR) is applied. For bulk magnetometry applications it is beneficial to excite large ensemble of NV centers at the same time since the minimum magnetic field that can be detected is proportional to 1/$\sqrt{N}$, where N is the total number of the probed NVs. Theoretical estimates predict that a magnetic sensor based on NV ensembles with NV densities of ≈10$^{15}$-10$^{17}$ cm$^{-3}$ distributed throughout the volume of mm$^3$ diamond sample would result in an ultra-high sensitivity at fT/$\sqrt{\text{Hz}}$ scales. For this to work, however, uniform magnetic fields over the whole sample volume are needed. Some microwave delivery techniques (e.g., based on a copper wire, loop antenna, or coplanar waveguide) can only address NV centers within a small range: for example ~30 µm and ~150 µm in the case of wire and loop antenna, respectively. To overcome this limitation, a resonator such as a double split-ring microwave resonator may be used, which can address NV centers over a relatively large volume (e.g., on the order of a few mm$^3$). Moreover, this approach increases the efficiency of microwave delivery and increases the strength of NV-microwave interaction (e.g., potentially by more than 8-fold).

Figure 1A:
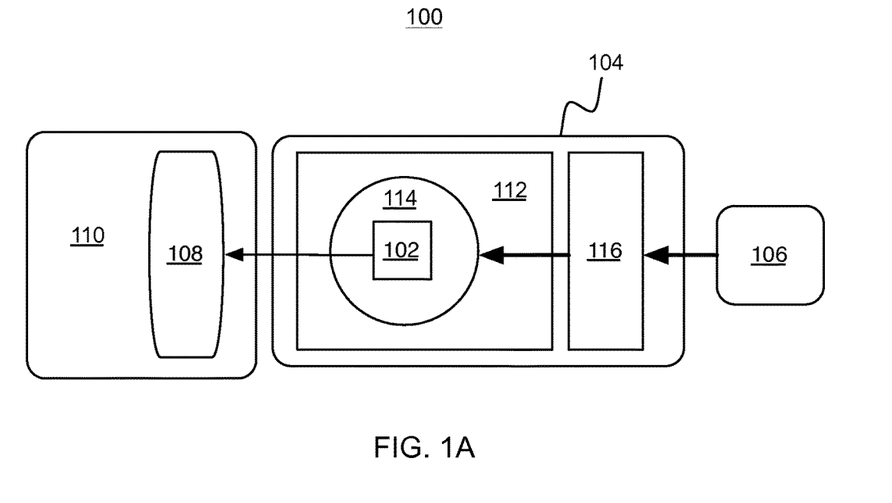
FIG. 1A is a schematic diagram of an ODMR imaging system.

FIG. 1A shows an example of an ODMR imaging system 100. The system 100 supports a sample 102 positioned on an ODMR device 104. The ODMR device 104 is coupled to a microwave source 106 that provides a microwave signal with desired bandwidth and amplitude characteristics (e.g., a pulsed microwave signal with a bandwidth matched to the bandwidth of the resonator 114). An optical detection subsystem 110 detects an optical output generated from the sample 102 during operation. The ODMR device 104 includes a substrate 112, such as a dielectric material, that houses an electromagnetic field resonator 114 that, in some implementations, is designed for operation over a microwave range of frequencies of the electromagnetic field within the resonator (i.e., between about 300 MHz and about 300 GHz). The resonator 114 is coupled to the microwave source 106 via a microwave coupler 116 that is part of the ODMR device 104.

In order to efficiently provide a highly uniform magnetic field, the resonator 114 is configured to include two or more resonant structures at least partially contained within the substrate 112. In implementations in which these resonant structures are conducting strip transmission lines shaped in the form of split rings (or other nearly closed shapes) within a non-conducting substrate, a magnetic field is generated in the middle of the structures as they surround a sample positioned within (or otherwise in proximity to) the inner resonant structure. The optical detection subsystem 110 includes an optical coupler 108 (e.g., a lens) positioned in proximity to the inner resonant structure, and configured to receive an output optical signal from the sample 102. The optical coupler 108 is also configured to provide an input optical signal to the sample 102. The output optical signal is generated based at least in part on the magnetic field generated by the resonator 114, and the input optical signal. The sample 102 is characterized by an electron spin resonance frequency (e.g., due to the NV centers). A range of an operating resonance frequency of the resonator 112 is at least partially determined by: (1) a size of an inner area of the inner resonant structure, and (2) the number of resonant structures that surround the inner resonant structure. The range for the operating resonance frequency is designed, by appropriate choice of geometric size parameters, to include the electron spin resonance frequency of the sample so that significant optical signal can be generated. In some implementations, the parameters are selected based in part on certain characteristics of the sample: material (e.g., single crystal diamond) or thickness (e.g., thin-film).

Figure 1B:
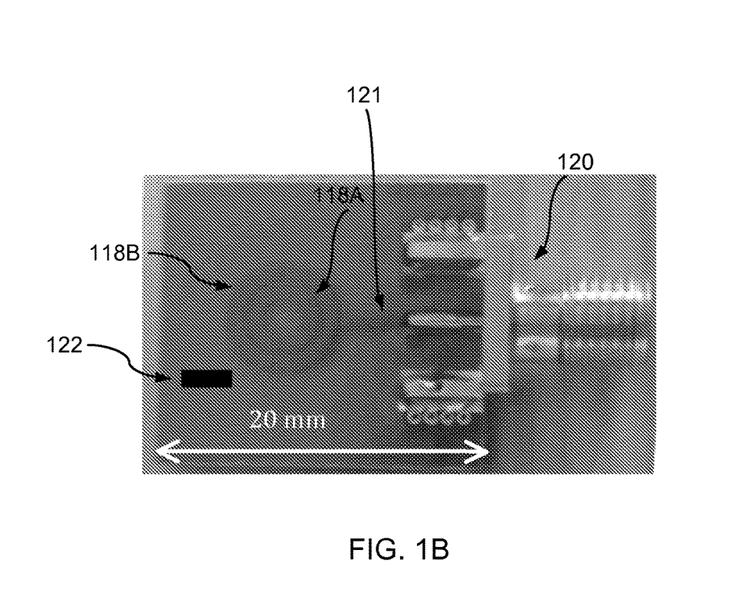
FIG. 1B is an image of a microwave coupler.

FIG. 1B shows an implementation of ODMR device 104 in which the resonator 114 is a double split-ring resonator and the substrate 112 is a printed circuit board (PCB). The double split-ring resonator is formed in this example by two magnetically coupled transmission lines shaped in the form of rings as two resonant structures 118A and 118B, which are terminated by respective gaps as shown in FIG. 1B. The microwave power is supplied via a 50Ω coaxial cable terminator 120 attached to a 50Ω microstrip line 121 as the microwave coupler 116, which is coupled to the double split-ring resonator through a capacitive gap that serves as an impedance matching element. A tuning element 122 is positioned in proximity to the resonant structure 118B (the outer ring). The tuning element 122 is configured to tune the operating resonance frequency of the resonator 114 within a tuning range, as described in more detail below.

The ODMR device 104 may be designed to enable a variety of operating modes. For example, the inner resonant structure may be configured to provide a magnetic field at the sample 102 positioned in proximity to a first side (e.g., bottom side) of the resonator 114, and the optical coupler 108 may be positioned in proximity to a second side (e.g., top side) of the resonator 114. In that way, the optical coupler 108 receives the output optical signal from the sample 102 through the opening in the inner resonant structure. The ODMR device 104 may be designed to allow the sample 102 to be positioned within a chamber, such as a cryogenic chamber.

In an implementation in which the microwave magnetic field has a frequency of 2.87 GHz, the surface of a 3 mm×3 mm diamond sample (0.5 mm thick) mounted on the resonator 114 would have a fairly uniform field distribution over a 1 mm$^2$ area of in the center of that surface.

The NV center is a point defect in diamond, which consists of a substitutional nitrogen neighboring a vacant lattice point. Negatively charged NV has an extra electron at the defect site resulting in paramagnetic properties. Due to the crystal field, the spin levels are split by 2.87 GHz, with $m_s=0$ in the lowest energy level, and the $m_s=\pm 1$ in the highest energy level. An external magnetic field lifts the degeneracy of $|\pm 1\rangle$ state with a Zeeman shift given by $\Delta m_s \gamma B_\|$, where $\gamma$ and $B_\|$ are the NV gyromagnetic ratio $\gamma = g\mu_B/h = 2.8$ MHz/G and projection of magnetic field along the NV symmetry axis, respectively. Thus, the NV's ESR frequency shifts in the presence of the external magnetic field.

Figure 2:
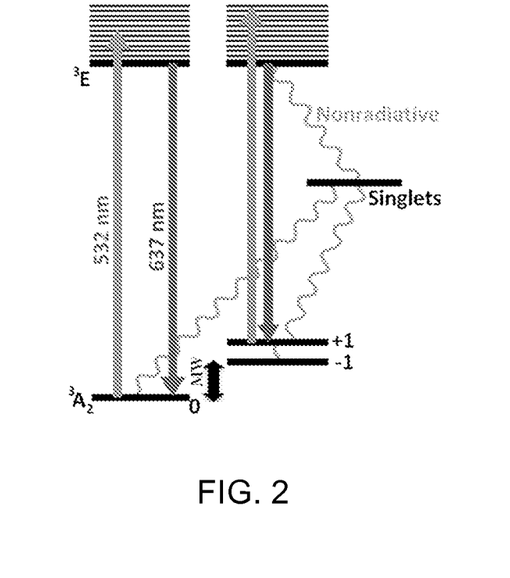
FIG. 2 is an energy band diagram of a negatively charged NV center.

FIG. 2 shows an energy band diagram 200 of a negatively charged NV center. Electronic spin polarization and readout is carried out by 532 nm (green) excitation and 638-800 nm (red) fluorescence detection. Spin manipulation in ground state triplet is performed by applying microwave power at ~2.87 GHz, zero magnetic field splitting.

Figure 3:
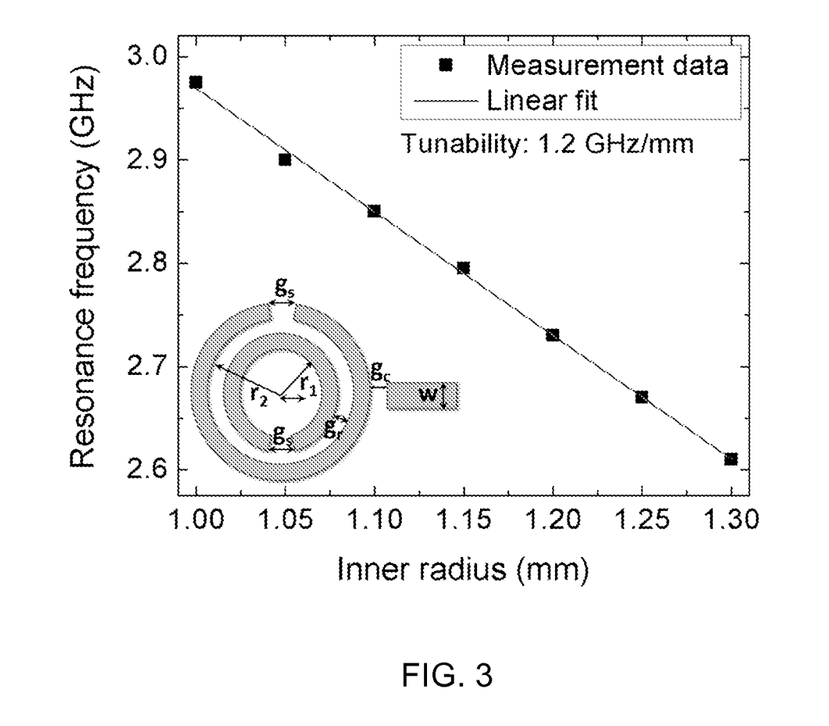
FIG. 3 is a plot of resonance frequency relative to inner radius, with a diagram showing resonator dimensions.

The design of the resonator 114 can be optimized (i.e., configured for use with a particular set of desired performance criteria) by setting appropriate design parameters of an analytical model using full-wave numerical simulations. Examples of optimized design parameters for the resonator 114 are shown in FIG. 3, which shows geometrical dimensions of the resonator 114 along with a plot of the measured resonance frequency of the resonator 114 as a function of inner radius parameter $r_1$. The plot includes measurement data points and a linear fit to those data points. The magnitude of $S_{11}$, known as the return loss of the resonator 114, highly depends on the size of the coupling gap ($g_c$). In order to reduce the return loss and increase the microwave power coupled to the resonator 114, the coupling gap size $g_c$ should be relatively small. In this example, the optimized coupling gap size was found to be 50 μm. The ratio between the electromagnetic energy stored in the resonator 114 and energy lost in one cycle, called the quality factor (Q), is inversely proportional to the sum of the Ohmic loss in metal wires of the ODMR device 104, the dielectric loss of the substrate 112, radiation loss resonator 114, and coupling loss of the microwave coupler 116. A large Q results in a large magnetic field intensity at the center of the resonator 114, at the expense of the reduced bandwidth (BW) and response time of the resonator 114. Therefore, some optimized resonator 114 designs would have low-Q and be critically coupled to the feeding microwave coupler 116.

Figure 4:
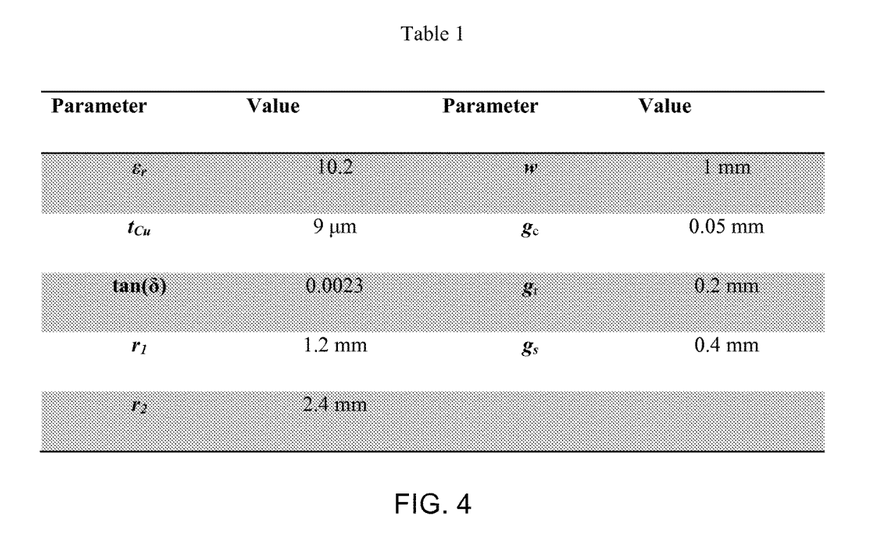
FIG. 4 is a table of geometrical dimension parameters of the resonator.
Figure 5A:
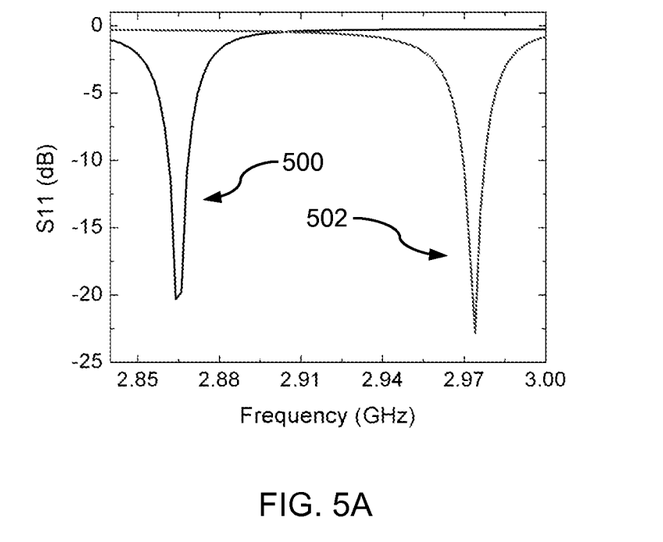
FIGS. 5A and 5B are plots of simulated and measured return loss spectra, respectively.

FIG. 4 shows Table 1, which lists the geometrical dimensions of the resonator 114 optimized for a very low $S_{11}$ of approximately −25 dB, a Q factor of ~120, and a resonance frequency of around 2.974 GHz. FIG. 5A shows a simulated $S_{ii}$ spectral response of the resonator 114 before and after placing a diamond sample 102 (dimensions 3 mm×3 mm×0.5 mm) at the middle of the resonator 114. The plots of the simlulated $s_{11}$ spectra of the resonator 114 include a loaded plot 500 (with the diamond sample in the resonator 114) and unloaded plot 502 (without the diamond sample in the resonator 114), over the frequency range of 2.85-3.00 GHz. It can be seen in FIG. 5A that the sample 102 results in a red shift of the resonance frequency of ~110 MHz, without affecting the quality factor significantly. The frequency shift is attributed to the changes in the effective dielectric constant of the resonator 114 due to the presence of the sample 102. The nine geometrical parameters listed in Table 1 were obtained from these simulations; where $r_1$ and $r_2$ are 1.2 mm and 2.4 mm, respectively. The nine parameters $\varepsilon_r$, $t_{cu}$, $\tan(\delta)$, $r_1$, $r_2$, w, $g_c$, $g_r$, $g_s$ are: dielectric constant of the substrate 112, thickness of the copper layer on the substrate 112 from which the rings are formed, loss tangent of the substrate 112 material, inner radius of the inner ring, inner radius of the outer ring, width of the microwave coupler 116, coupling gap between the outer ring and the microwave coupler 116, gap between the rings, and gap size at the split of each ring, respectively. The thicknesses of the two rings, which are identical, can be derived from the parameters $r_1$, $r_2$, $g_r$, as $r_2$-$r_1$-$g_r$.

Figure 5B:
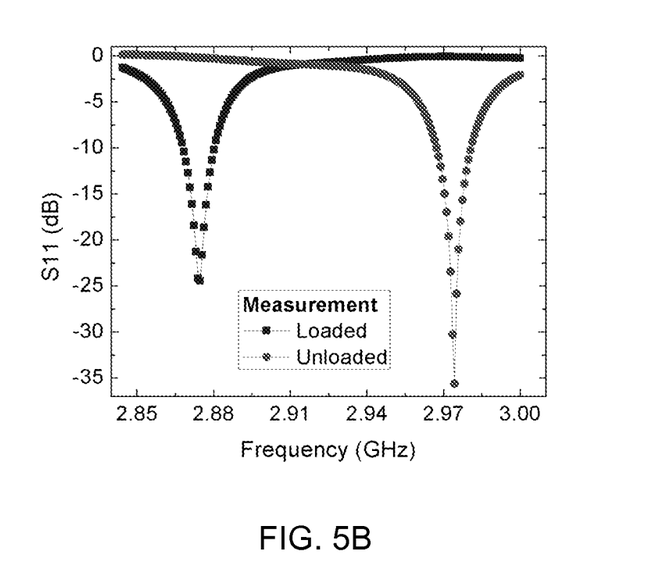

FIG. 5B shows plots of experimentally measured $S_{11}$ spectra of the resonator 114 loaded (with the diamond sample) and unloaded (without diamond sample) over the same frequency range of 2.85-3.00 GHz. A single crystal electronic grade diamond sample, with the dimensions of 3 mm×3 mm×0.5 mm, was used in these experiments. The inner radiuses of inner and outer rings for the experiments was $r_1$=1 mm and $r_2$=2.2 mm, respectively.

Based on a field intensity simulation, the distribution of the normal component of the magnetic field intensity at the top surface of the diamond sample 102 was fairly uniform, with an average of $H_z$=354.8 A/m, and an average of $B_z$=4.46 G, for an input power of $P_{in}$=1 W. The variation of $H_z$ along x, y and z directions over 1.5 mm×1.5 mm area and thickness of 0.5 mm were less than 6.5%, 10% and 1%, respectively. The stored electromagnetic energy in the resonator 114 can be found as $(1-S_{11}^2)QP_{in}/\omega_r$, where $p_{in}$ represents the input microwave power delivered to the resonator 114 and $\omega_r$ represents the resonance frequency of the resonator 114. As a consequence, the magnitude of the magnetic field intensity at any point with coordinates (x,y,z) inside the resonator 114 can be given by $C(x,y,z) \sqrt{(1-S_{11}^2)QP_{in}/\omega_r}$. $C(x,y,z)$ takes into account spatial distribution of the magnetic field, and also depends on the geometry and material composition of the resonator 114. In this example, given the uniform field distribution, we can use approximation $C(x,y,z) \approx C(x_c,y_c,z_{PCB})$, which is the value at the center of the resonator 114 at the PCB/diamond interface. Based on the field intensity simulation, we get $C(x_c,y_c,z_{PCB})$=5.48×10$^4$ G/√J. This can be used to make estimates of the magnetic field for a given input microwave power.

The resonance frequency of the resonator 114 can be tuned over a wide range, for example, by controlling the inner radius $r_1$ of the inner ring, keeping the ring widths and the gap between them fixed. To confirm this experimentally, 10 resonator devices, with different inner radius, were fabricated, and characterized by a Network Analyzer. The plot of the resonance frequencies of fabricated resonators are shown FIG. 3, as a function of $r_1$. These results show that by changing $r_1$ from 1 mm to 1.3 mm, the resonant frequency can be varied between 2.6-2.97 GHz. Moreover, the resonance frequency is linearly dependent on inner radius of the resonator 114 with a slope of −1.153 GHz/mm.

Based on the measurements of FIG. 5B the operational parameters of the unloaded resonator 114 are: a resonance frequency of f=2.974 GHz, a return loss $S_{11}$~−35 dB, a quality factor Q=72, and a bandwidtdh BW=40 MHz. Using these parameters, we estimate that 99.97% of the input power at center resonance frequency directly couples to the resonator 114 and contributes to the enhanced stored electromagnetic field in the system 100. The $S_{11}$ spectrum of loaded resonator 114, after placing a diamond sample with dimensions of 3×3×0.5 mm$^3$ on top of it, reveals the resonance frequency f=2.874 GHz, return loss of $S_{11}$~−25 dB, quality factor Q=70 and bandwidth BW=40 MHz. A red shift in the resonance frequency of 100 MHz is in good agreement with simulation results shown in FIG. 5A.

In order to use the resonator 114 for Optically Detected Magnetic Resonance (ODMR) applications, it is important to be able to tune its resonance frequency to the NV's ESR frequency. This fine-tuning can be achieved, for example, by using a strip of copper tape of a selected size placed close to the outer ring of the resonator 114 as the tuning element 122. The resonance frequency can be tuned without affecting the Q significantly. A variety of types of stubs and strips for frequency tuning microwave circuitry may be used as the tuning element 122. In this example, the copper tape affects the capacitive coupling between the outer ring and the ground plane (backside of the PCB) and hence shifts the resonance frequency. In one resonator configuration, a copper tape of 1.5×1.5 mm$^2$ in size can tune the resonance frequency within a 400 MHz window depending upon the positioning of the tape. For fine-tuning, the resonator 114 is connected to the Network Analyzer and the size and location of the copper tape is varied to achieve the desired center frequency. Using this approach, we were able to shift the resonant frequency from 2.874 GHz to 2.87 GHz (ESR resonance of NV), and perform further characterization of the system 100, as discussed below.

Figure 6:
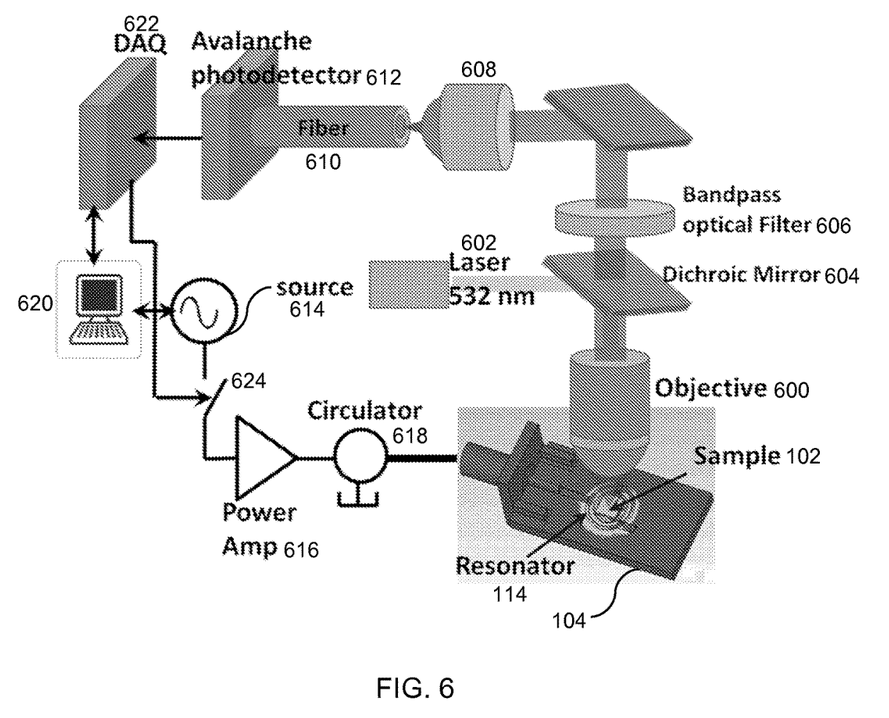
FIG. 6 is a schematic diagram of the ODMR imaging system with elements of the optical detection subsystem.

FIG. 6 shows an example implementation of the ODMR imaging system 100, in which the optical detection subsystem 110 includes a scanning confocal microscope as the optical coupler 108 illustrated in FIG. 6 by its objective 600. The optical detection subsystem 110 also includes a laser 602 providing an input optical siganl at a wavelength of 532 nm, and an optical detection path after the objective 600 that includes a dichroic mirror 604, a bandpass optical filter 606, a collimating lens 608, an optical fiber 610, and an avalanche photodetector 612. The microwave source 106 is illustrated in FIG. 6 by a power source 614, a power amplifier 616, and a circulator 618, connected by a coaxial cable to the microwave coupler 116 of the ODMR device 104. A computer 620 controls a digital acquisition (DAQ) cuircuit board 622 that interfaces with a signal from the avalanche photodetector 612, and interfaces with the power source 614. The DAQ circuit board 622, under control of the computer 620, also provides a signal to open and close a switch 624 that powers the ODMR device 104 on and off.

The Rabi nutation frequencies of respective nanowire patches on a diamond sample were measured using this implementation of the system 100. Considering the 30 dB gain of the amplifier, and the −3 dB loss of the microwave switch and isolator, the actual power fed to the resonator 114 is 0.5 W resulting in the Rabi nutation frequency of 16.69 MHz. This is nearly an order of magnitude larger than frequencies (~1.8 MHz) typically achieved using a loop antenna or a copper wire for microwave delivery (instead of the resonator 114), for the same input power. The component of magnetic field perpendicular to the NV symmetry axis, $B_1$, can be calculated from the Rabi nutation frequency, $\Omega$, using the following equation: $\Omega=\gamma B_1$. The measured values of Rabi nutation frequency and $B_1$ for different nanowire patches were fairly uniform over the entire measurement area (0.95 mm×1.2 mm): Rabi frequency is in the range of 14.34-16.69 MHz (standard deviation of 0.68 MHz) while $B_1$ is in the range of 5.13-5.96 G (standard deviation of 0.24 G and normalized standard deviation of 4.4%). This confirms that the resonator 114 delivers a uniform magnetic field over a mm$^2$ area scale, as predicted by full wave numerical analysis.

It is to be understood that the foregoing description is intended to illustrate and not to limit the scope of the invention, which is defined by the scope of the appended claims. Other embodiments are within the scope of the following claims. For example, some embodiments use samples measured using other types of magnetic resonance interactions.

What is claimed is:

1. An apparatus comprising:
   a substrate that includes a dielectric material;
   an electromagnetic-field resonator that includes two or more resonant structures at least partially contained within the dielectric material, at least a first resonant-structure being configured to provide a magnetic field at a sample positioned in proximity to the first resonant structure, the sample being characterized by an electron-spin resonance-frequency, wherein a size of an inner area of the first resonant-structure and a number of resonant structures included in the electromagnetic-field resonator at least partially determine a range of an operating resonance-frequency of the electromagnetic-field resonator that includes the electron-spin resonance-frequency; and
   an optical coupler positioned in proximity to the first resonant-structure and configured to receive an output optical-signal from the sample, the output optical-signal being generated based at least in part on a magnetic field generated by the electromagnetic-field resonator,
   wherein the first resonant structure is configured to provide a magnetic field at the sample positioned in proximity to a first side of the electromagnetic-field resonator and
   wherein the optical coupler is positioned in proximity to a second side of the electromagnetic-field resonator and is configured to receive the output optical-signal from the sample through an opening defined by the first resonant-structure.

2. The apparatus of claim 1, further comprising a tuning element configured to tune the operating resonance-frequency of the electromagnetic-field resonator within the range.

3. The apparatus of claim 2, wherein the first resonant-structure is configured to at least partially surround the sample within the inner area of the first resonant-structure.

4. The apparatus of claim 1, wherein the range of the operating resonance-frequency includes at least some microwave frequencies.

5. The apparatus of claim 1, wherein the size of the inner area provides a uniformity of the magnetic field generated by the electromagnetic-field resonator within about 10% or less over an area of the sample of about one square millimeter or more.

6. The apparatus of claim 1, wherein the two or more resonant structures comprise two or more split rings.

7. The apparatus of claim 1, wherein the substrate comprises a printed circuit board.

8. The apparatus of claim 1, further comprising an optical coupler configured to receive an output optical-signal from the sample, the output optical-signal being generated based at least in part on a magnetic field generated by the electromagnetic-field resonator.

9. The apparatus of claim 8, wherein the optical coupler is further configured to provide an input optical-signal to the sample.

10. The apparatus of claim 1, further including a microwave coupler configured to couple a microwave signal into the electromagnetic-field resonator.

11. The apparatus of claim 10, further including a microwave source configured to provide a pulsed microwave-signal to the microwave coupler, with a bandwidth of the pulsed microwave signal being within a bandwidth of the electromagnetic-field resonator.

12. The apparatus of claim 11, further comprising a tuning element configured to tune the bandwidth of the electromagnetic-field resonator.

13. The apparatus of claim 12, wherein the tuning element comprises a material that changes a quality factor of the electromagnetic-field resonator.

14. The apparatus of claim 1, wherein the sample comprises diamond and wherein the electron-spin resonance-frequency is based on nitrogen-vacancy centers in the diamond.

15. The apparatus of claim 1, wherein the sample comprises a thin-film material.

16. The apparatus of claim 1, wherein the sample is positioned within a cryogenic chamber.

17. A method for measuring a sample, the method comprising:
   providing a magnetic field at the sample using an electromagnetic-field resonator including two or more resonant structures at least partially contained within dielectric material of a substrate, at least a first resonant structure configured to provide the magnetic field at the sample positioned in proximity to the first resonant structure, the sample being characterized by an electron-spin resonance-frequency, wherein a size of an inner area of the first resonant structure and a number of resonant structures included in the electromagnetic-field resonator at least partially determine a range of an operating resonance frequency of the electromagnetic-field resonator that includes the electron-spin resonance frequency; and
   receiving an output optical signal from the sample using an optical coupler positioned in proximity to the first resonant structure, the output optical signal being generated based at least in part on a magnetic field generated by the electromagnetic-field resonator,
   wherein the first resonant-structure is configured to provide a magnetic field at the sample positioned in proximity to a first side of the electromagnetic-field resonator and
   wherein the optical coupler is positioned in proximity to a second side of the electromagnetic-field resonator and is configured to receive the output optical-signal from the sample through an opening defined by the first resonant-structure.

18. The method of claim 17, further comprising positioning the sample within a cryogenic chamber.

* * * * *